(12) United States Patent
Doyle et al.

(10) Patent No.: US 10,017,726 B2
(45) Date of Patent: Jul. 10, 2018

(54) ULTRASONIC METHOD WITH SHORT PULSES FOR MONITORING MONOLAYERS OF CULTURED CELLS

(75) Inventors: Timothy E Doyle, Springville, UT (US); Soonjo Kwon, Providence, UT (US); Hemangkumar J Patel, Gujarat (IN); Jeffrey B. Goodrich, North Logan, UT (US)

(73) Assignee: Utah State University, North Logan, UT (US)

(*) Notice: Subject to any disclaimer, the term of this patent is extended or adjusted under 35 U.S.C. 154(b) by 265 days.

(21) Appl. No.: 13/296,036

(22) Filed: Nov. 14, 2011

(65) Prior Publication Data

US 2012/0122140 A1  May 17, 2012

Related U.S. Application Data

(60) Provisional application No. 61/413,458, filed on Nov. 14, 2010.

(51) Int. Cl.
*C12M 1/34* (2006.01)

(52) U.S. Cl.
CPC .................. *C12M 41/46* (2013.01)

(58) Field of Classification Search
None
See application file for complete search history.

(56) References Cited

U.S. PATENT DOCUMENTS

| | | |
|---|---|---|
| 2005/0148899 A1 | 7/2005 | Walker et al. |
| 2007/0167778 A1 | 7/2007 | Crowley et al. |
| 2009/0089025 A1 | 4/2009 | Doyle et al. |

FOREIGN PATENT DOCUMENTS

| | | |
|---|---|---|
| WO | WO9615446 | 5/1996 |
| WO | WO2012065151 | 5/2012 |

OTHER PUBLICATIONS

Holmes, "Ultrasonic Imaging of Biofilms Utilizing Echoes from the Biofilm/Air Interface," IEEE Transactions On Ultrasonics, Ferroelectrics, And Frequency Control, vol. 53, p. 185-192, 2006.*
Shemesh, "High frequency ultrasound imaging of a single-species biofilm," J Dentistry, vol. 35, p. 673-678, 2007.*
Czarnota, "Ultrasound imaging of apoptosis: high-resolution non-invasive monitoring of programmed cell death in vitro, in situ and in vivo," British Journal of Cancer, vol. 81, p. 520-527, 1999.*
Brand, "Monitoring Of Cell Death In Epithelial Cells Using High Frequency Ultrasound Spectroscopy," Ultrasound in Med. & Biol., vol. 35, p. 482-493, 2009.*
Doyle et al., Ultrasonic differentiation of normal versus malignant breast epithelial cells in monolayer cultures, 128 (5) J. Acoust. Soc. Am. (Oct. 19, 2010).
Doyle et al., Ultrasonic modeling and measurements of cultured normal and malignant breast epithelial cells, 2nd Pan-American/Iberian Meeting on Acounstics, Nov. 15-19, 2010, Cancun Mexico. Abstract published online J. Acoust. Soc. Am., vol. 128, No. 4, Pt. 2 (Oct. 6 2010).
International Search Authority and Written Opinion for PCT/US2011/060514, dated Feb. 27, 2012.

* cited by examiner

*Primary Examiner* — G. Steven Vanni
(74) *Attorney, Agent, or Firm* — Kunzler, PC

(57) ABSTRACT

A method for monitoring a cell culture, where the method includes measuring pulse-echo ultrasonic waveforms from the cell culture, and analyzing the pulse-echo ultrasonic waveforms to monitor the cell culture.

11 Claims, 11 Drawing Sheets

ULTRASONIC METHOD WITH SHORT PULSES FOR MONITORING MONOLAYERS OF CULTURED CELLS

RELATED APPLICATIONS

This application claims the benefit under 35 U.S.C. 119(e) of U.S. Provisional Patent Application No. 61/413,458, filed Nov. 14, 2010, and entitled "ULTRASONIC METHOD FOR MONITORING CELL CULTURES," which is incorporated by reference in its entirety.

GOVERNMENT SPONSORED RESEARCH

This invention was made with government support under contract R21 CA131798 awarded by the National Institutes of Health. The government has certain rights in the invention

TECHNICAL FIELD

The present disclosure relates to an ultrasonic pulse-echo detection method to non-invasively monitor biological cell cultures.

BACKGROUND

Current methods to measure cell growth, properties, and other parameters in cell cultures include microscopic cell counting methods, image analysis methods applied to microphotographs to estimate cell size, sacrifice of the cell culture to count cells in a hemacytometer, and atomic force microscopy (AFM) to measure cell stiffness. However, new and additional methods of performing these functions are needed.

SUMMARY

The above methods are frequently labor intensive, require multiple laboratory personnel to conduct the analyses, are time consuming, can be expensive such as the cost of AFM probe tips for analyses, and are frequently invasive or destructive, requiring sacrifice of the cell culture for analysis. These deficiencies result in low efficiency, high cost, and low throughput, as well as poor statistical sampling of the cell cultures. Therefore, methods are needed to rapidly, accurately, and non-invasively monitor cell cultures.

In addition, the ability to measure a range of properties in biological cell cultures is important for various applications, including but not limited to biomedical, microbiological, bioengineering, and tissue engineering research and applications. Examples of such applications include the following:

The capability to rapidly, non-invasively, and quantitatively measure the growth of malignant cell cultures undergoing testing with chemotherapy agents;

The discrimination between cancerous and non-cancerous cells during studies of tumorigenesis and tumor progression in biological tissues;

The monitoring of cell properties, tissue structure, and growth rate in the engineering and culture of artificial organs;

The rapid, nondestructive detection and characterization of bacterial biofilms on surfaces outside of a laboratory environment;

Integrated, high-throughput testing of pharmaceutical and other bioactive agents on cell cultures.

The present disclosure in aspects and embodiments addresses these various needs and problems by providing methods, and associated devices, for monitoring a cell culture, which comprise measuring pulse-echo ultrasonic waveforms from the cell culture, and analyzing the pulse-echo ultrasonic waveforms to monitor the cell culture.

BRIEF DESCRIPTION OF THE DRAWINGS

Understanding that drawings depict only certain embodiments of the invention and are therefore not to be considered limiting of its scope, the preferred embodiments will be described and explained with additional specificity and detail through the use of the accompanying drawings.

Components include a high-frequency ultrasonic transducer, a high-frequency ultrasonic pulser-receiver, a method to digitize the ultrasonic signal (a digital oscilloscope in this example), and a method to store and process the data (a laptop personal computer in this example).

Figure 2:
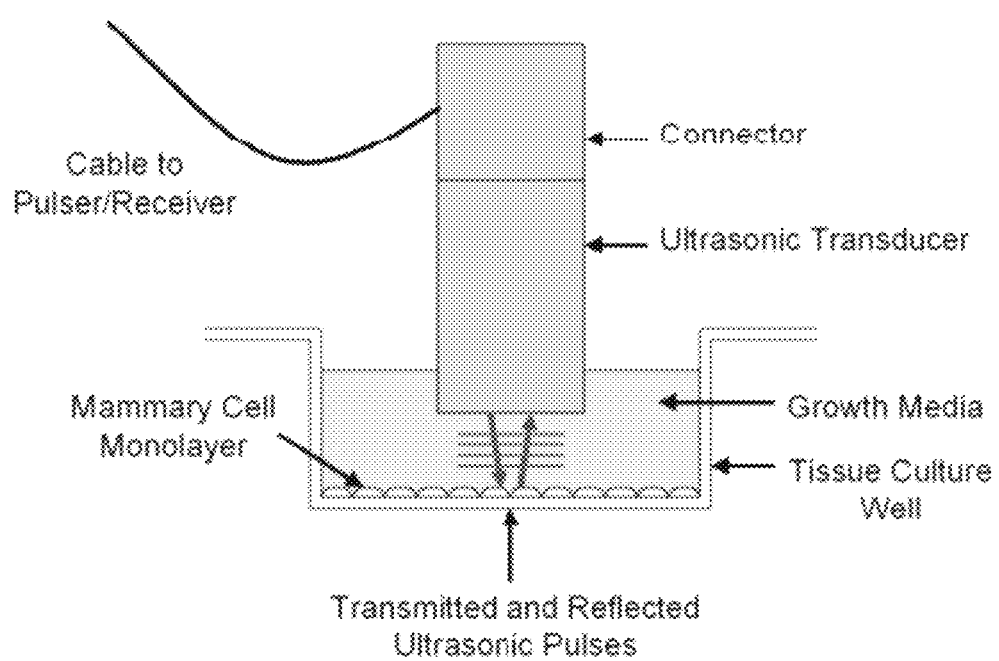

FIG. 2 illustrates an exemplary ultrasonic measurement setup for monitoring the growth and properties of cell cultures. In this example, the cell culture is a breast cell monolayer grown in a tissue culture well of a culture well plate.

Figure 3:
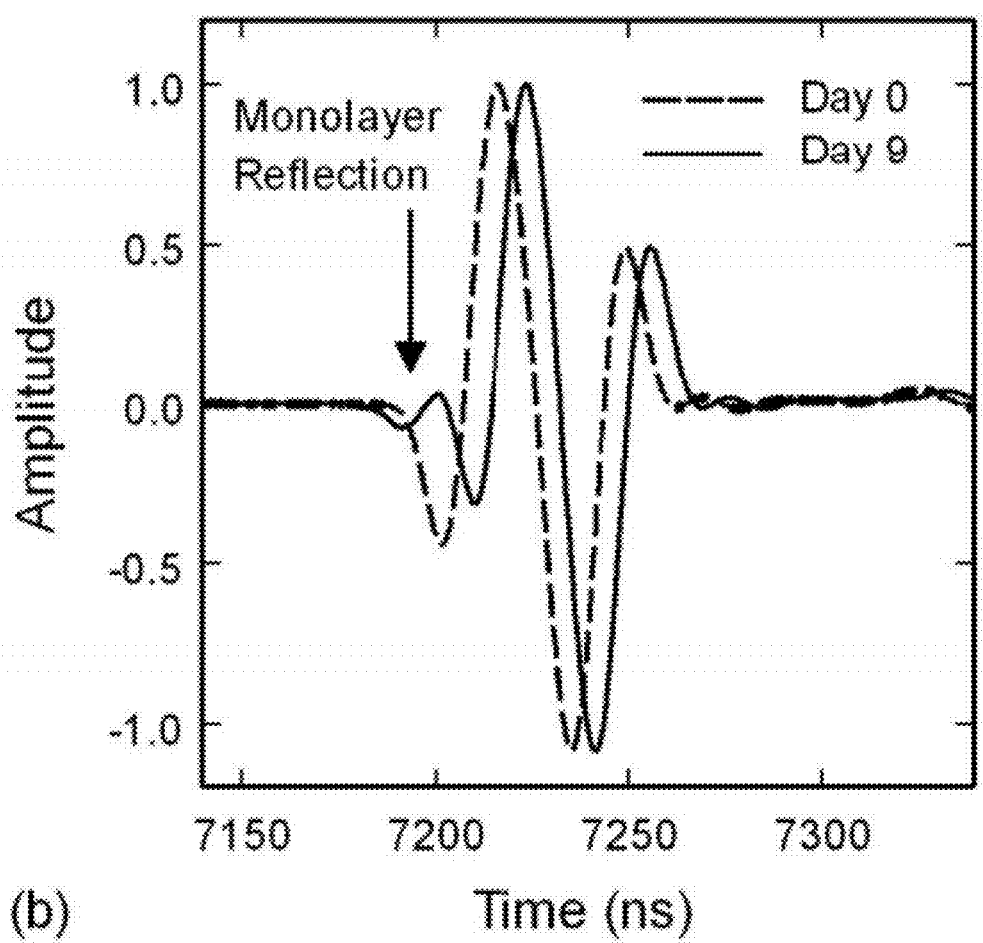

FIG. 3 shows an exemplary comparison of ultrasonic waveforms for a tissue culture well with no cell monolayer (Day 0, dashed) and with a cell monolayer covering 100% of the tissue culture well surface (Day 9, solid). Cell layer reflection occurs at approximately 7200 ns on Day 9 waveform (arrow). Waveforms are offset in time for clarity.

Figure 4:
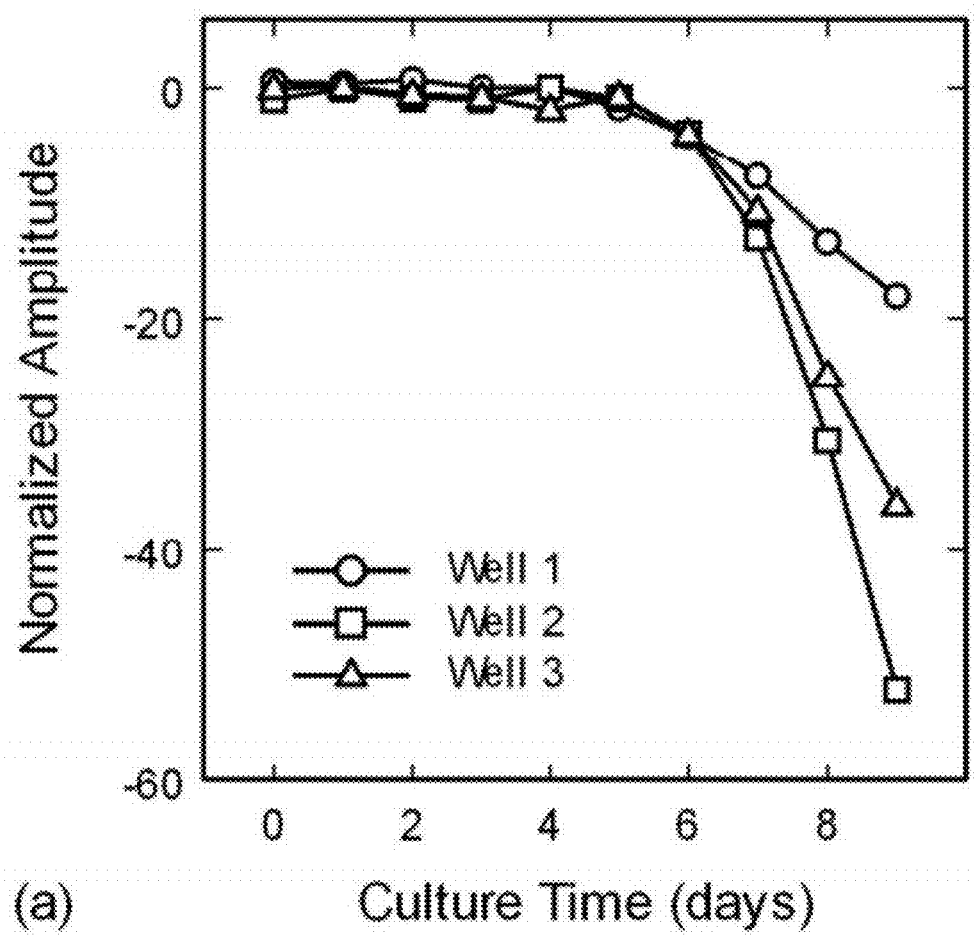

FIG. 4 shows an exemplary ultrasonic signal amplitude for the ultrasonic reflection from normal breast epithelial cells as a function of culture time, showing a good correlation to the cell growth (coefficient of correlation=−0.90).

Figure 5:
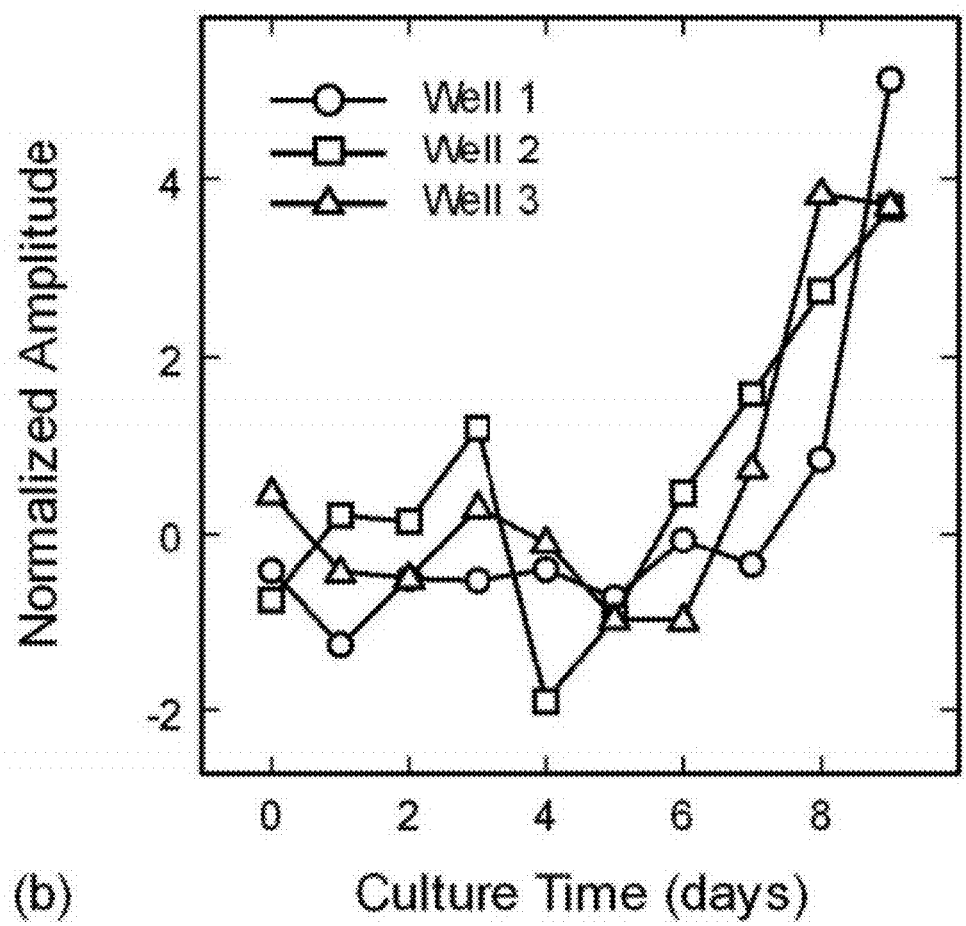

FIG. 5 shows an exemplary ultrasonic signal amplitude for the ultrasonic reflection from malignant breast epithelial cells as a function of culture time, showing a good correlation to the cell growth (coefficient of correlation=0.76).

Figure 6:
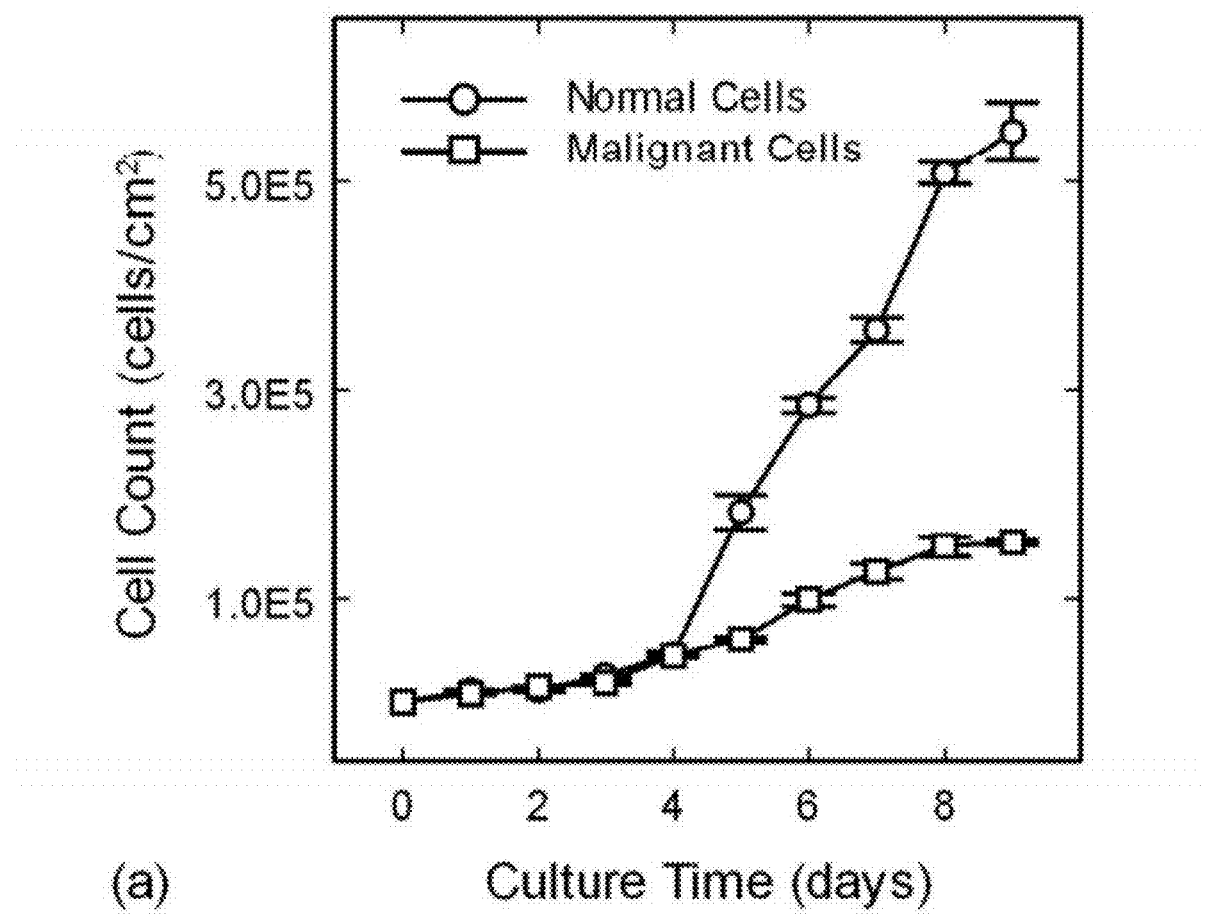

FIG. 6 shows an exemplary growth rate for normal and malignant breast epithelial cells as measured with a hemacytometer.

Figure 7:
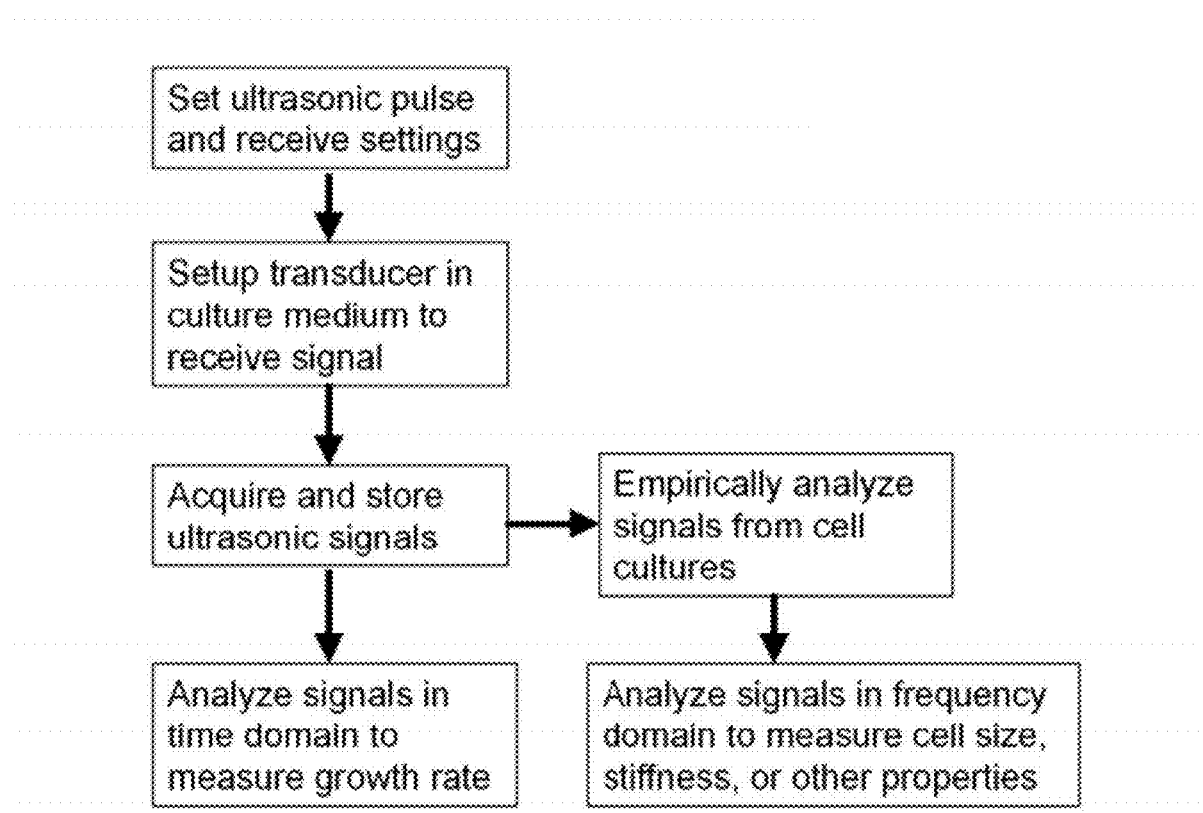

FIG. 7 shows exemplary process steps for measuring and analyzing the ultrasonic data using an empirical approach.

Figure 8:
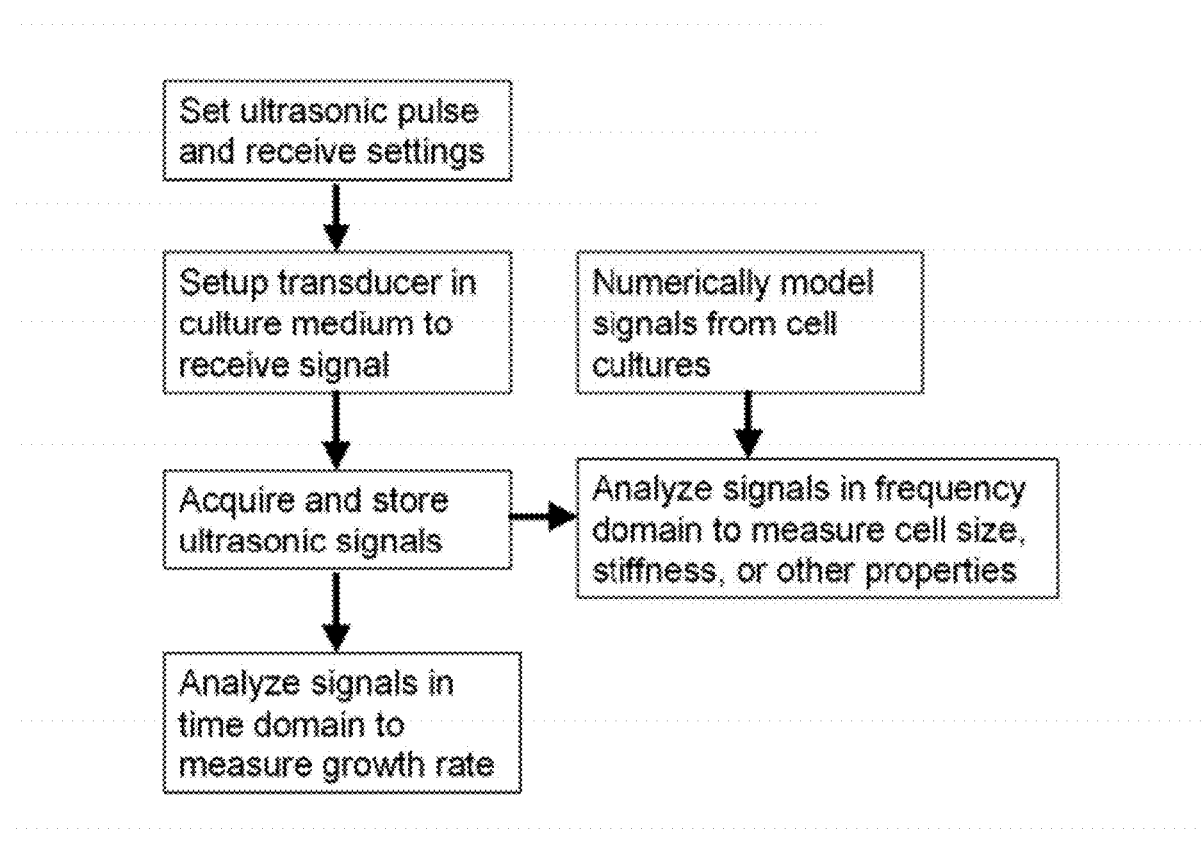

FIG. 8 shows exemplary process steps for measuring and analyzing the ultrasonic data using a model-based approach.

Figure 9:
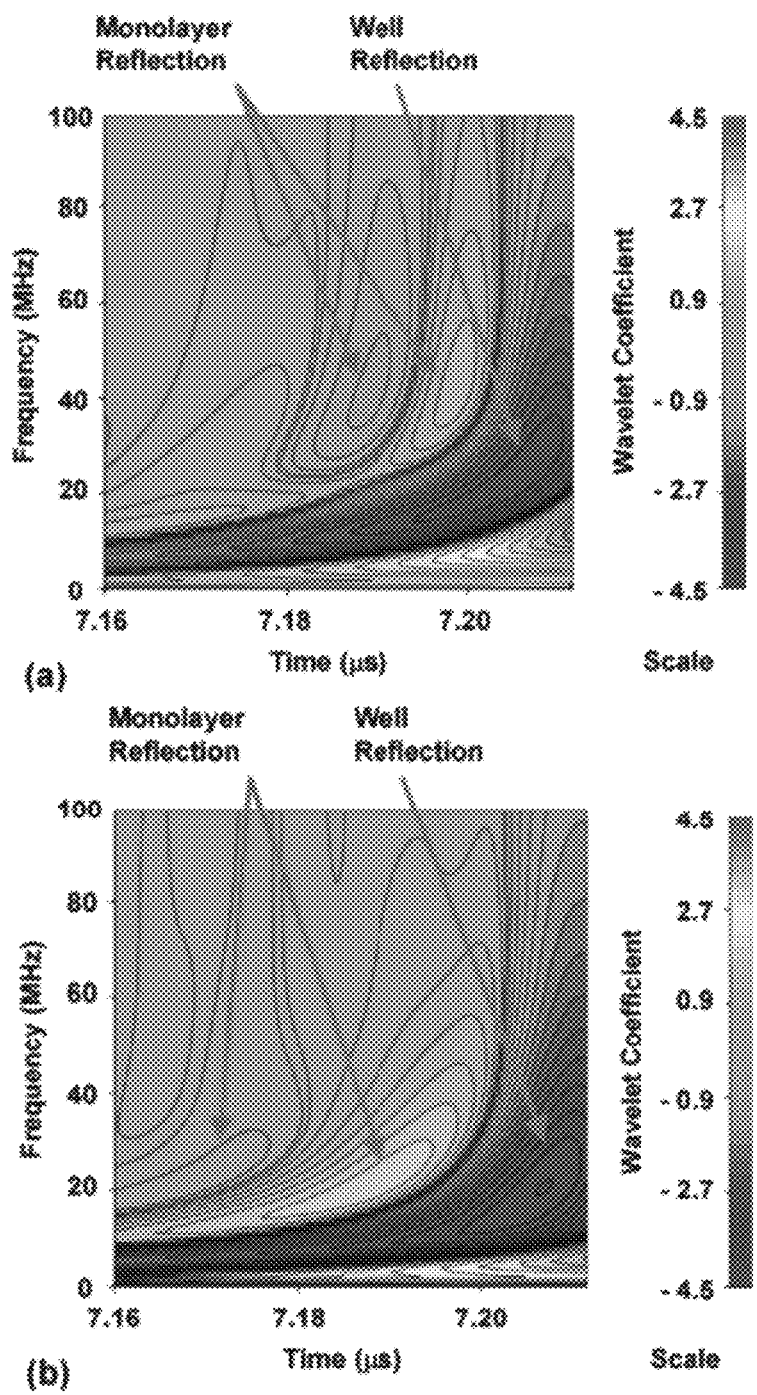

FIG. 9 shows an exemplary wavelet analysis used to identify the differences in frequency content between the reflections of the normal cell monolayer and the malignant cell monolayer.

Figure 10:
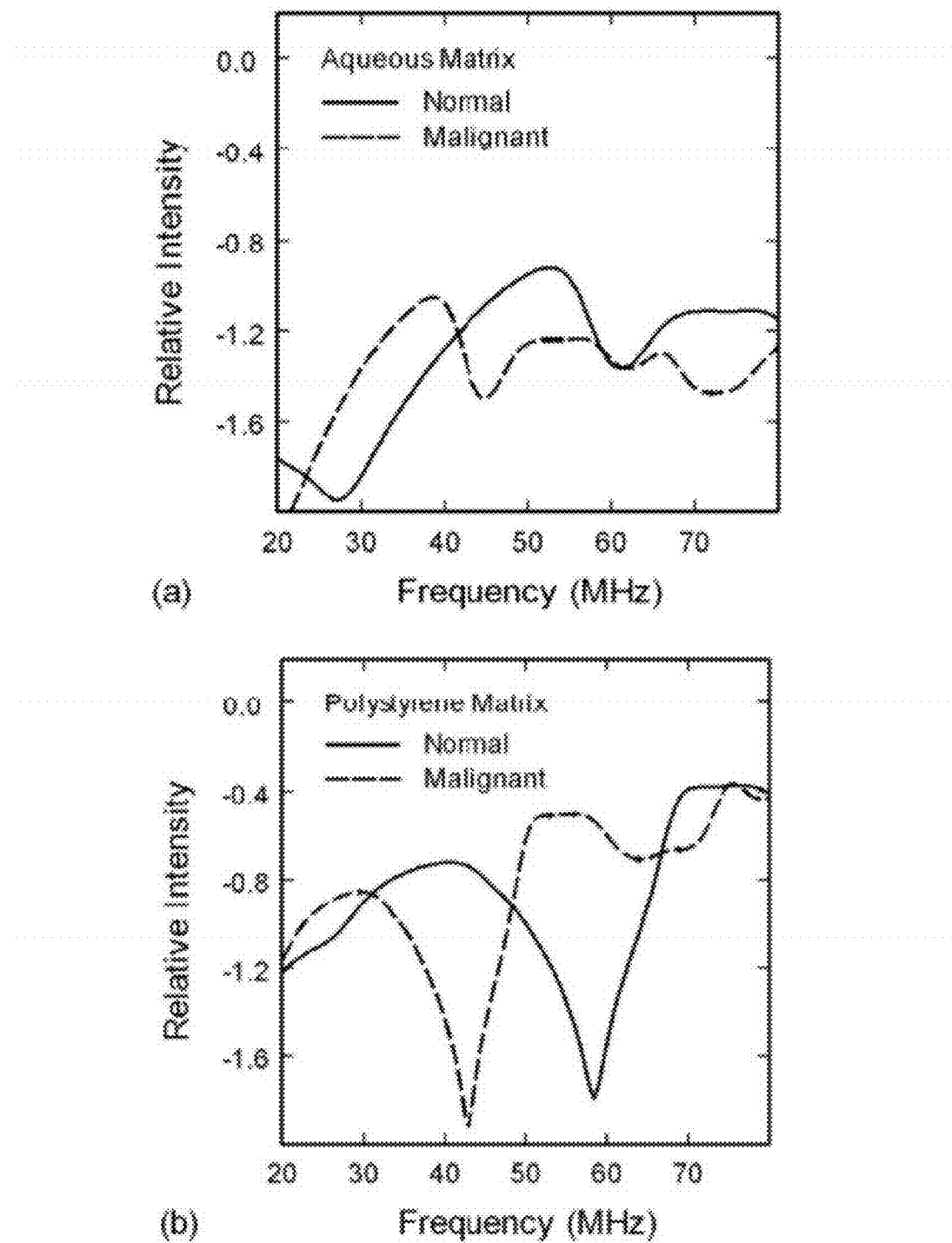

FIG. 10 shows exemplary, predicted ultrasonic spectra from a multipole-based numerical model of a monolayer of spherical cells in water (a) and in the culture well material, polystyrene (b). The models predict that malignant breast epithelial cells will display ultrasonic signals at a lower frequency than their normal counterparts.

Figure 11:
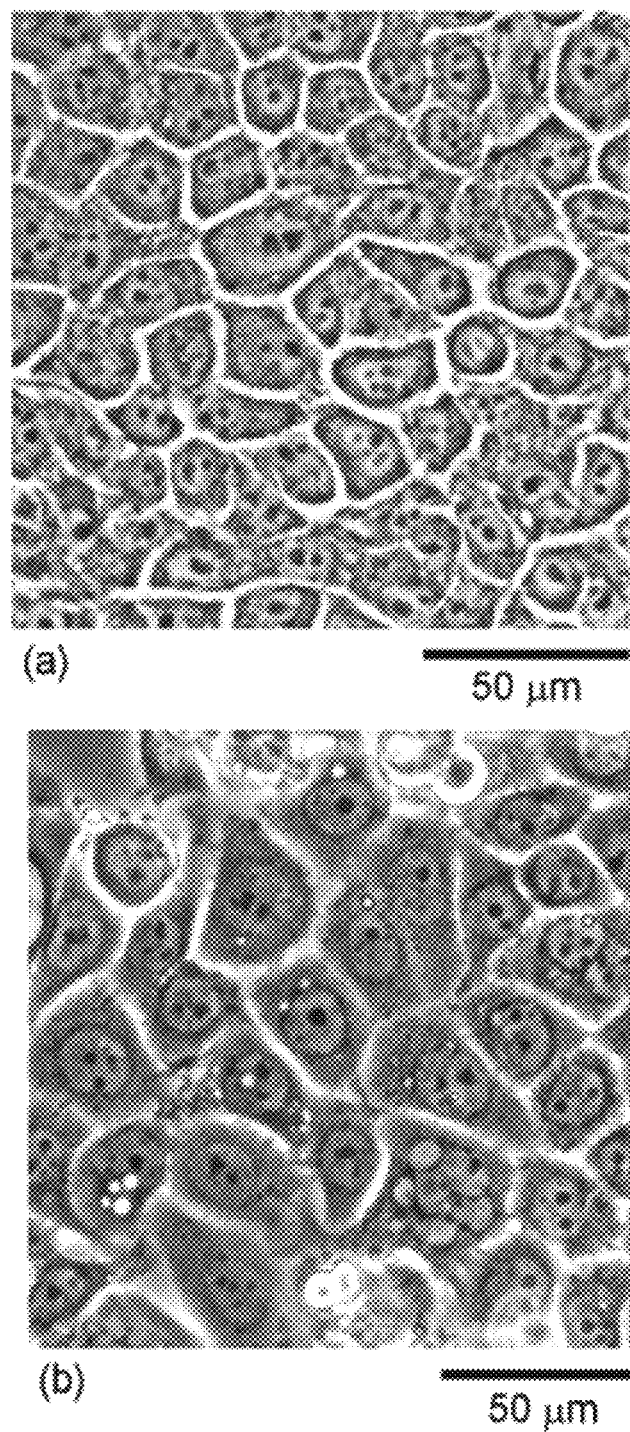

FIG. 11 shows exemplary micrographs of the normal (a) and malignant (b) epithelial cells, indicating the differences in cell size.

DETAILED DESCRIPTION

The present disclosure covers apparatuses and associated methods for monitoring cell cultures. In the following description, numerous specific details are provided for a thorough understanding of specific preferred embodiments. However, those skilled in the art will recognize that embodiments can be practiced without one or more of the specific details, or with other methods, components, materials, etc. In some cases, well-known structures, materials, or operations are not shown or described in detail in order to avoid obscuring aspects of the preferred embodiments. Furthermore, the described features, structures, or characteristics may be combined in any suitable manner in a variety of alternative embodiments. Thus, the following more detailed description of the embodiments of the present invention, as illustrated in some aspects in the drawings, is not intended to limit the scope of the invention, but is merely representative of the various embodiments of the invention.

In this specification and the claims that follow, singular forms such as "a," "an," and "the" include plural forms unless the content clearly dictates otherwise. All ranges disclosed herein include, unless specifically indicated, all endpoints and intermediate values. In addition, "optional" or "optionally" refer, for example, to instances in which subsequently described circumstance may or may not occur, and include instances in which the circumstance occurs and instances in which the circumstance does not occur. The terms "one or more" and "at least one" refer, for example, to instances in which one of the subsequently described circumstances occurs, and to instances in which more than one of the subsequently described circumstances occurs.

The present disclosure describes acoustic methods and associated devices for non-invasively monitoring the growth and properties of biological cell cultures. The methods may be applicable any suitable type of cell culture, such as, for example, cell monolayers, cell cultures with multiple layers, three-dimensional cell cultures, cell co-cultures, engineered tissues, and microbial thin films. Any suitable cell may be monitored, including, for example, prokaryotic cells, eukaryotic cells, bacteria, mammalian cells, and human cells.

The methods comprise measuring pulse-echo ultrasonic waveforms from the cell cultures and analyzing the waveforms both in the time and frequency domains to characterize the cultures and/or identify features relating to the associated cells that are useful for determining their type, condition, state of growth, and/or pathology.

Figure 1:
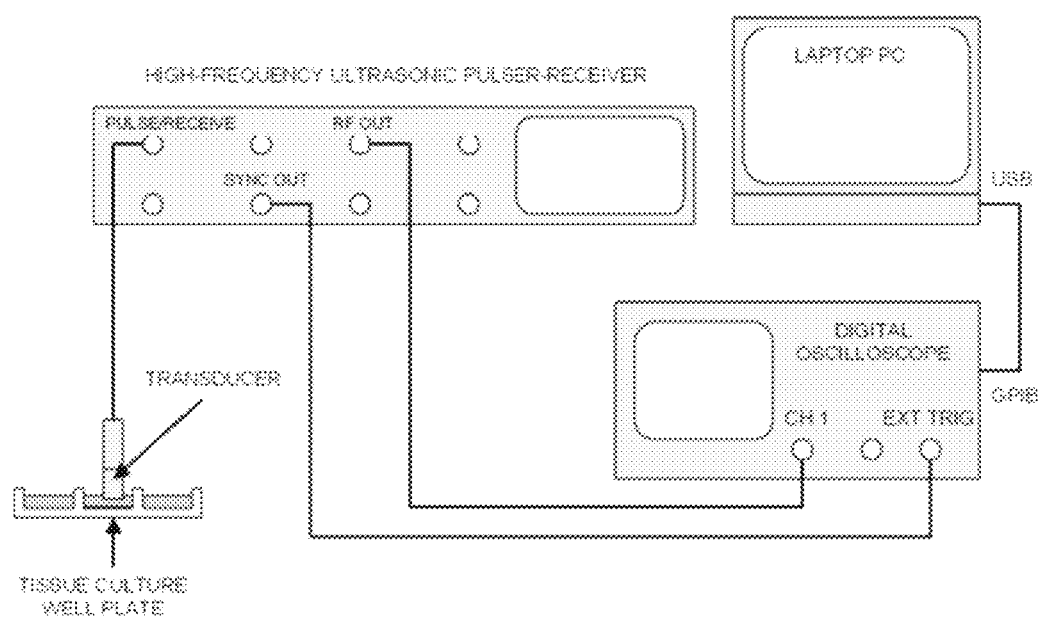
FIG. 1 displays an example of the type of ultrasonic equipment used for monitoring the growth and properties of cell cultures. In this example, the cell culture is a breast cell monolayer grown in a tissue culture well of a culture well plate.

Any suitable high-frequency (about 10-100 MHz) pulser-receiver with a broadband, high-frequency immersion transducer or transducer array may be used to measure the pulse-echo ultrasonic waveforms. The pulser-receiver may be either custom-built equipment or off-the-shelf equipment such as used for standard nondestructive or medical testing (See, e.g., FIG. 1).

In some embodiments, a monitoring device comprises a pulser-receiver coupled to a data analyzing module capable of storing data from the pulser-receiver and/or analyzing and processing the stored data to monitor the cell-culture. The monitoring device may be capable of measuring pulse-echo ultrasonic waveforms from the cell cultures and analyzing the waveforms both in the time and frequency domains to characterize the cultures. The monitoring device may also perform the specific steps and functions described herein.

Waveforms may be acquired by immersing a transducer in the cell culture or the growth media of the cell culture; pulsing the transducer with a spike pulse or square-wave pulse at a suitable frequency, such as at the transducer's peak frequency; and collecting at least one reflection. This may include a surface reflection from the substrate on which the cell culture is growing, such as a polystyrene cell culture well plate (See, e.g., FIG. 2). Depending on the state of growth of the cell culture, this waveform may also contain a surface reflection from the cell culture (a cell culture reflection) immediately preceding the substrate reflection in the time-domain waveform (See, e.g., FIG. 3).

The amplitude of the cell culture reflection (See, e.g., FIGS. 4 and 5) may be linearly correlated to the growth (number of cells) of the cell culture in time (See, e.g., FIG. 6). The spectral properties of the cell culture reflections may also be related to properties of the cell cultures, including the average size, density, and compressive stiffness (bulk modulus) of the cell and nucleus. These properties may be obtained either by an empirical approach (See, e.g., FIG. 7), where multiple measurements from cell cultures are acquired and their ultrasonic signatures correlated with other analytical data, or by model-based approach (See, e.g., FIG. 8), where the ultrasonic wave reflections from the cells are modeled by one or more of various numerical or effective medium methods.

The following examples are illustrative only and are not intended to limit the disclosure in any way.

EXAMPLES

Time-domain analysis of ultrasonic waveform reflections. Breast epithelial cells were cultured for up to 9 days and then analyzed with the method described herein to determine the ultrasonic signal differences between normal and malignant cells. In this example, the ultrasonic waveform for Day 9 displayed a distinct wave structure in front of the well reflection, with an initial valley and then a peak (See FIG. 3). This additional reflection feature may be attributed to the normal epithelial cell monolayer since it is absent from the Day 0 ultrasonic waveform.

The amplitudes of the time-domain ultrasonic waveforms were analyzed to determine the state of cell culture growth. The normal cells displayed an initial valley in the waveforms (negative amplitude), whereas the malignant cells displayed an initial peak in the waveform (positive amplitude). The amplitude curves for the normal cells showed a smooth trend for each well, but diverged significantly from well to well with culture time (See FIG. 4). In contrast, the trends for the malignant cells were not smooth and showed greater day-to-day variations for each well (See FIG. 5). However, the malignant cell trends did not diverge as strongly with culture time. The amplitude curves for the normal and malignant cell cultures showed a good correlation with cell growth as measured by a hemacytometer (See FIG. 6), with correlation coefficients of −0.90 and 0.76, respectively.

Frequency-domain analysis of ultrasonic waveforms. Because the ultrasonic reflections from the cell culture monolayers were of much less amplitude than the primary reflection from the surface of the well plate, their frequency components might be somewhat difficult to discern from traditional spectral analyses using methods, such as the fast Fourier transform. A wavelet analysis was therefore performed to extract the frequency components of the waveforms as a function of both frequency and pulse reflection time. This allowed the frequency components of the cell monolayer reflections to be separated from the frequency components of the polystyrene well reflection.

A wavelet analysis of the waveforms indicated that the primary frequency component of the well reflection was 23 MHz, but that the principal frequencies for the normal and malignant cell layer reflections were 40 MHz (See FIG. 9a) and 20 MHz (See FIG. 9b), respectively.

Model-based analysis of frequency-domain results. The spectral data analyses may be interpreted using either empirical approaches or computational simulations of ultrasonic scattering from the cell cultures. The computational simulations may include a multilayer pulse-reflection model, a model of two-dimensional arrays of spherical cells and nuclei, and other appropriate simulations. An example of the two-dimensional arrays of spherical cells containing spherical nuclei to simulate a cell monolayer follows. In this example, multipole expansions and boundary conditions were used to solve for the acoustic scattering from each cell. Backscattered wave fields are then summed at the transducer face to calculate the measured ultrasonic amplitude. Other examples of computational approaches include multilayer reflection models, finite element models, finite-difference time-domain models, and boundary element models.

For cells in a water-based culture medium, the multipole model showed that the primary spectral peak for the normal cell monolayers was shifted 14 MHz higher in frequency as compared to the malignant cell monolayers due to the smaller size of the normal cells (See FIG. 10a). For cells on a polystyrene matrix such as a culture well, the resulting spectra (See FIG. 10b) showed a downward shift in the primary spectral peaks from 53 to 40 MHz for the normal cells and from 39 to 31 MHz for the malignant cells. Additional simulations revealed that the spectra were also sensitive to the shear properties of the cytoplasm. The differences in the spectra between the normal and malignant cells may be attributed to the larger size of the malignant cells (average diameter=32.6±10.3 µm) as compared to the normal cells (average diameter=21.6±6.9 µm), as shown in FIG. 11.

The results show that normal and malignant epithelial cells may be distinguished by isolating and identifying their spectral signatures with the use of wavelet analysis and numerical simulation. The wavelet analysis isolates the spectral signatures of the cells from other features in the waveform, such as the well reflection, and identifies their principal frequencies. The numerical simulation correlates the spectral signatures and principal frequencies with features that distinguish the normal and malignant cells, such as their size.

This method allows for the rapid and automated monitoring of cell growth in cultures without sacrificing samples or requiring tedious microscopic counting methods. It also provides cell size information and information not currently available by present techniques such as the density and elastic properties of the cells. Other information may also be extracted such as properties of the cells' extracellular matrix, cell morphology, and live versus dead cells.

Applications for the method include, for example, the fields of biomedical research; drug research, development, and production by pharmaceutical companies; and improved process monitoring for microbe-based production processes.

It will be appreciated that various of the above-disclosed and other features and functions, or alternatives thereof, may be desirably combined into many other different systems or applications. Also, various presently unforeseen or unanticipated alternatives, modifications, variations or improvements therein may be subsequently made by those skilled in the art, and are also intended to be encompassed by the following claims.

What is claimed is:

1. A method for monitoring physical properties of cells in a cell monolayer, through measuring pulse-echo ultrasonic waveforms from the cell monolayer with a pulser-receiver, the method comprising:
   presenting a cell monolayer;
   immersing a transducer in a liquid that is in contact with the monolayer;
   pulsing the transducer with a pulse of less than 100 nanosecond duration, wherein the pulse produces constructive interference among scattered waves from the cells in the monolayer, thereby producing in the liquid plane wave reflections having parallel wavefronts;
   collecting at least one monolayer reflection;
   analyzing the pulse-echo ultrasonic waveforms and thereby measuring one or more physical properties of the cells wherein the physical properties comprise average nuclear size and optionally one or more of average cell size, average cell and/or nuclear density, compressive stiffness of the cell and/or nucleus and shear stiffness of the cell and/or nucleus.

2. The method of claim 1, wherein the at least one plane wave reflection comprises at least one of a substrate reflection from a substrate which supports the monolayer and a reflection from the surface of the monolayer.

3. The method of claim 2, wherein the reflection from the surface of the monolayer immediately precedes the substrate reflection in a time-domain waveform.

4. The method of claim 1, wherein the analysis of the pulse-echo ultrasonic waveforms comprises an analysis of at least one of time and frequency domains to characterize the monolayer.

5. The method of claim 1, wherein the analysis of the pulse-echo ultrasonic waveforms comprises a spectral data analysis.

6. The method of claim 5, wherein the analysis of the pulse-echo ultrasonic waveforms comprises frequency-domain analysis.

7. The method of claim 6, wherein the frequency-domain analysis comprises wavelet analysis to extract frequency components of waveforms as a function of both frequency and pulse reflection time.

8. The method of claim 5, wherein the spectral data analysis is interpreted using a model based computational simulation approach.

9. The method of claim 8, wherein the model is selected from the group consisting of a multilayer pulse-reflection model and a multipole model.

10. The method of claim 1, further comprising linearly correlating frequency spectrums of monolayer reflections and thereby measuring the physical properties of the cells and/or using a computational simulation approach and thereby measuring physical properties of the cells wherein the computational simulation approach comprises a model of two dimensional assemblages of cells and nuclei.

11. A method for monitoring a cell monolayer through measuring pulse-echo ultrasonic waveforms from the monolayer with a pulser-receiver, the method comprising:
   presenting a cell monolayer selected from the group consisting of cell cultures, cell co-cultures, engineered tissues, and cells extracted from tissues and configured into a monolayer;
   immersing a transducer in a liquid that is in contact with the monolayer;
   pulsing the transducer with a pulse, of less than 100 nanoseconds duration, such that an ultrasonic plane wave is produced in the liquid creating a surface reflection from the monolayer;
   pulsing the transducer with a pulse of less than 100 nanosecond duration, such that a surface reflection from the monolayer returns as an additive, coherent signal, with in-phase wavefronts;

collecting the monolayer surface reflections as time and frequency domain measurements at intervals ranging from one or more nanoseconds to one or more days, with automated data acquisition; and analyzing the pulse-echo ultrasonic waveforms and thereby monitoring the monolayer with a data analyzing module, wherein the analysis comprises linearly correlating amplitudes of monolayer reflections and thereby measuring the growth of the monolayer in time and/or using a computational simulation approach and thereby measuring one or more physical properties of the cells, wherein the physical properties comprise average nuclear size and optionally one or more of average cell size, average cell and/or nuclear density, compressive stiffness of the cell and/or nucleus and shear stiffness of the cell and/or nucleus.

* * * * *